US008554480B2

(12) United States Patent
Grigsby et al.

(10) Patent No.: US 8,554,480 B2
(45) Date of Patent: Oct. 8, 2013

(54) TREATMENT DATA PROCESSING AND PLANNING SYSTEM

(75) Inventors: Jean Grigsby, Downingtown, PA (US); Madelyn McGillin, Wayne, PA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 3682 days.

(21) Appl. No.: 10/870,584

(22) Filed: Jun. 17, 2004

(65) Prior Publication Data

US 2005/0215867 A1  Sep. 29, 2005

Related U.S. Application Data

(60) Provisional application No. 60/556,418, filed on Mar. 25, 2004.

(51) Int. Cl.
*G06Q 10/00* (2012.01)
*G06Q 50/00* (2012.01)

(52) U.S. Cl.
USPC .................................................. 702/2; 705/3

(58) Field of Classification Search
USPC ........................................................ 705/2, 3, 20
See application file for complete search history.

(56) References Cited

U.S. PATENT DOCUMENTS

| | | | |
|---|---|---|---|
| 5,786,816 A | 7/1998 | Macrae et al. | |
| 5,832,448 A * | 11/1998 | Brown | 705/2 |
| 6,277,071 B1 | 8/2001 | Hennessy et al. | |
| 6,338,039 B1 | 1/2002 | Lonski et al. | |
| 2002/0095313 A1 | 7/2002 | Haq | |
| 2002/0120187 A1 * | 8/2002 | Eiffert et al. | 600/407 |
| 2002/0120471 A1 | 8/2002 | Drazen | |
| 2003/0036923 A1 | 2/2003 | Waldon et al. | |
| 2003/0055679 A1 | 3/2003 | Soll et al. | |
| 2003/0171659 A1 | 9/2003 | Dean | |
| 2004/0002873 A1 | 1/2004 | Sachdeva | |
| 2004/0024616 A1 | 2/2004 | Spector et al. | |

FOREIGN PATENT DOCUMENTS

| WO | WO 00/78374 A1 | 12/2000 |
|---|---|---|
| WO | WO 02/099600 A2 | 12/2002 |

OTHER PUBLICATIONS

International Search Report, Dec. 29, 2005.
System Analysis: Software and Hardware Design of the Automated Patient Medical Record System http://222.uprforum.com/Chap13.htm, 2001.

* cited by examiner

*Primary Examiner* — Robert Morgan
*Assistant Examiner* — Charles P Coleman
(74) *Attorney, Agent, or Firm* — Joshua B Ryan

(57) ABSTRACT

A patient treatment management system involves a repository including treatment information for a particular patient identifying treatment objectives and an associated schedule for achievement of the objectives. An interface processor acquires data representing clinical information of a particular patient related to a particular treatment objective. A monitoring processor assesses from the acquired clinical information whether the particular treatment objective is achieved substantially by a scheduled time deadline. A task scheduling processor automatically initiates scheduling of a first sequence of tasks to be performed by a healthcare worker in response to a determination the treatment objective is achieved and initiates scheduling of a different second sequence of tasks to be performed by a healthcare worker in response to a determination the treatment objective is not achieved.

20 Claims, 6 Drawing Sheets

US 8,554,480 B2

TREATMENT DATA PROCESSING AND PLANNING SYSTEM

This is a non-provisional application of provisional application Ser. No. 60/556,418 by J. Grigsby et al. filed Mar. 25, 2004.

FIELD OF THE INVENTION

This invention concerns a system for managing patient treatment and associated healthcare worker tasks.

BACKGROUND INFORMATION

Existing healthcare treatment planning systems require continual manual observation, intervention, and documentation of treatment outcomes and comparison of outcomes with expected or desired treatment objectives. Variances indicating a variation of patient treatment from planned treatment are identified and recorded in a patient treatment plan. The management of expected outcomes and variances within a Treatment Plan requires constant vigilance and documentation by healthcare provider personnel (nurses, physicians, managers etc.) involved in the treatment plan. Existing systems require significant manual intervention by a healthcare worker to manage care plans. The time and burden involved in managing a treatment plan deters use of standardized care plans because healthcare providers give greater priority to hands on patient care than to care documentation. Therefore, much documentation is done retrospectively and is often incomplete or incorrect. Further, in a health care environment there is often pressure to reduce staff to patient ratios and this is hampered by a need to provide such comprehensive documentation in a timely manner due to the manual intervention and associated resources involved. An automated system according to invention principles provides treatment plan management and addresses these problems and associated problems.

SUMMARY OF THE INVENTION

An automated system provides treatment plan monitoring, analysis and variance processing and adaptively selects and schedules workflow tasks in response to an identified variance indicating a variation of patient treatment or outcome from a planned treatment or outcome. A patient treatment management system involves a repository including treatment information for a particular patient identifying treatment objectives and an associated schedule for achievement of the objectives. An interface processor acquires data representing clinical information of a particular patient related to a particular treatment objective. A monitoring processor assesses from the acquired clinical information whether the particular treatment objective is achieved substantially by a scheduled time deadline. A task scheduling processor automatically initiates scheduling of a first sequence of tasks to be performed by a healthcare worker in response to a determination the treatment objective is achieved and initiates scheduling of a different second sequence of tasks to be performed by a healthcare worker in response to a determination the treatment objective is not achieved.

DETAILED DESCRIPTION OF INVENTION

Figure 1:
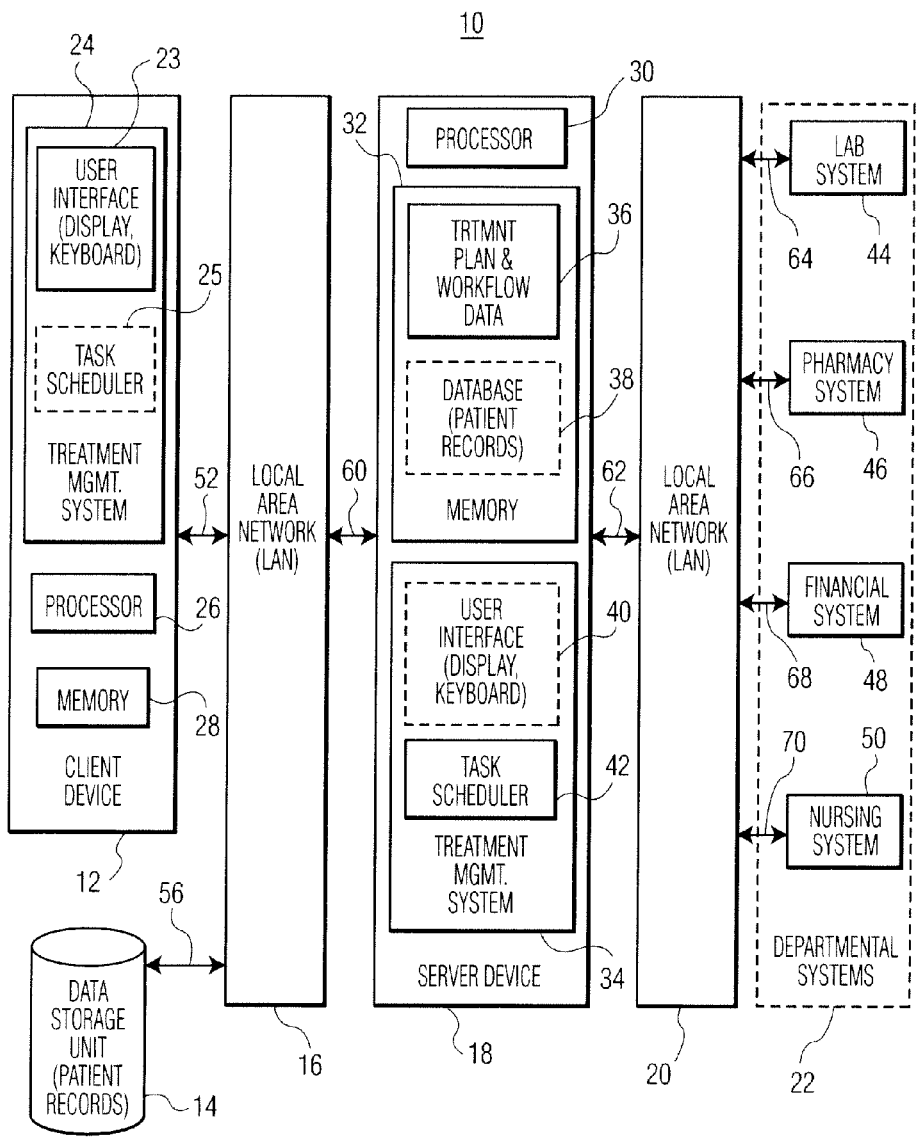
FIG. 1 shows a networked hospital information system including a patient treatment management system, according to invention principles.

FIG. 1 shows a networked hospital information system including a patient treatment management system 34. Automated treatment management system 34 manages care plan analysis, variance processing and associated documentation to ensure compliance of patient care with a plan. System 34 allocates standardized treatment goals and variance codes (identifying a variation of patient treatment from planned treatment). This increases a healthcare provider organizations ability to produce meaningful reports, and to determine best practices models. System 34 automatically monitors delivery of treatment to a plan and variations from plan and generates alerts based on such variations enabling patient care to be reassessed in a more timely manner, thus reducing risk and lowering cost by ensuring use of appropriate care plans. System 34 manages quality, safety, outcomes, variances, and resources (manpower and supplies) and reduces the documentation burden on healthcare providers enabling greater amounts of time to be spent on direct patient care. Treatment variances, their description, follow-up and analysis determine effectiveness of Treatment Plan implementation. System 34 processes treatment-variances and reduces the documentation burden on users as an integral part of care by supporting charting by exception and adaptive tailoring and refinement of Treatment Plans.

System 34 reduces manual involvement by a health care provider in reviewing, assessing and documenting progress against a plan of treatment stored in unit 36. System 34 automates evaluations and variance documentation within a standardized Treatment Plan. Workflow rules in unit 36 accommodate critical paths and decision points of a Treatment Plan, and any data point that is outside a defined normal range is able to trigger alerts that are sent to appropriate personnel and generate alternate workflow processes. System 34 documents a treatment variance with a predefined variance code. The rules in unit 36 are established when a standardized Treatment Plan Template is created and are modified and edited to accommodate individual patient needs. A typical Treatment Plan consists of desired goals (expected outcomes) and actions (care) a healthcare team need to take to reach these expected outcomes. Actions represent ordered services including: assessments, physical care, procedures, tests, and interventions. Target timeframes are assigned to goals and actions taken by a healthcare provider. A deviation from achieving an expected goal and completing an action is termed a variance. System 34 provides a function that can assist with real time, process control of treatment and associated processes and treatment actions.

As used herein, a processor comprises any one or combination of, hardware, firmware, and/or software. A processor acts upon information by manipulating, analyzing, modifying, converting or transmitting information for use by an executable procedure or an information device, and/or by routing the information to an output device. A processor may use or comprise the capabilities of a controller or microprocessor, for example. A display generator is a known element comprising electronic circuitry or software or a combination of both for generating display images or portions thereof.

System 34 supports standardized treatment plan templates, standardized goals, coded variances, automatic alerts for goals not met, notification to appropriate Healthcare providers for review of abnormal studies, generation of alternate routes for administering medication (automatic generation of orders for further studies) documentation of coded variances for reporting. Patients with high risk and complex care plans are monitored via the use of a Clinical information system Rules Engine and Workflow Engine (task scheduler 42). The rules accommodate the critical paths and decision points within a plan. Alerts are sent to appropriate personnel when procedures critical to the pathway have not been completed. Such an alert may reveal prompt discovery of an abnormal set of test results, patient parameters and images or an abnormal medical condition or may indicate that the required patient tests, parameters or images or treatments have not been completed by a predetermined deadline time. As a result of this monitoring and alerts, patient care is reassessed in a timely manner. The clinical information system provides an automated and accurate mechanism for managing quality, safety, outcomes, variances, and resources (manpower and supplies).

System 34 is integrated and cooperates with, a Clinical information system Rules Engine and Workflow Engine (task scheduler 42) to automatically monitor patient treatment and particularly monitor patients with high risk and complex care plans. The rules are generated to accommodate the critical treatment paths of a care plan and associated decision points, and a patient parameter data point that is outside a defined normal range initiates generation of an alert message that is sent to appropriate personnel, e.g., when procedures critical to a treatment pathway have not been completed or require immediate intervention.

FIG. 1 illustrates a healthcare information system 10 including a patient treatment plan monitoring system 34 and/or 24, in accordance with a preferred embodiment of the present invention. The healthcare information system 10 generally includes a client device 12, a data storage unit 14, a first local area network (LAN) 16, a server device 18, a second local area network (LAN) 20, and departmental systems 22. The healthcare information system 10 is used by a healthcare provider that is responsible for monitoring the health and/or welfare of people in its care. Examples of healthcare providers include, without limitation, a hospital, a nursing home, an assisted living care arrangement, a home health care arrangement, a hospice arrangement, a critical care arrangement, a health care clinic, a physical therapy clinic, a chiropractic clinic, and a dental office. In the preferred embodiment of the present invention, the healthcare provider is a hospital. Examples of the people being serviced by the healthcare provider include, without limitation, a patient, a resident, and a client.

The client device 12 generally includes a patient treatment plan monitoring system 24, a processor 26, and a memory unit 28. The treatment plan monitoring system 24 preferably includes a user interface 23 and a task scheduler 25, but may also include the processor 26 and the memory unit 28. The client device 12 is preferably implemented as a personal computer. The processor 26 and the memory unit 28 are constructed and operate in a manner well known to those skilled in the art of the design of client devices.

The user interface 23 in the client device 12 generally includes an input device that permits a user to input information into the client device 12 and an output device that permits a user to receive information from the client device 12. Preferably, the input device is a keyboard and mouse, but also may be a touch screen or a microphone with a voice recognition program, for example. The output device is a display, but also may be a speaker, for example. The output device provides information to the user responsive to the input device receiving information from the user or responsive to other activity by the client device 12. For example, the display presents information responsive to the user entering information in the client device 12 via the keyboard.

The task scheduler 25 in the client device 12 adaptively selects and schedules workflow tasks in response to a variance indicating a variation of patient treatment from planned treatment identified by patient treatment monitoring system 24. The task scheduler 25 is preferably implemented in software, but may also be implemented in hardware or a combination of both. Patient treatment plan monitoring system 24 in a preferred embodiment is located in server 18 as system 34 as an alternative to being located in client device 12 as system 24 The location of system 34 in server device 18 permits multiple users to have access to the same patient treatment plan monitoring system 34 from multiple client devices.

The data storage unit 14 stores patient records, as well as other information for the hospital information system 10. Preferably, the data storage unit 14 is separate from the client device 12 to permit multiple users to have access to the patient records in the data storage unit 14 from multiple client devices. The data storage unit 14 is separate from the server device 18 because of the physical size of the memory required to store the desired information. The data storage unit 14 may be implemented as read only memory (ROM), such as on a compact disk (CD) or on a hard drive, or a random access memory (RAM), and the like, as is well know to those skilled in the art of data storage units. Alternatively, the patient records may be stored in the database 38 in the memory unit 32 in the server device 18, as shown in dashed lines, in the memory unit 28 in the client device 12, or in memory units in the departmental systems 22, as the memory size becomes physically smaller, has increased capacity and becomes less expensive. An additional consideration would be the advantages and disadvantages of having the patient records stored in a single centralized memory unit or stored in several decentralized memory units among the data storage unit 14, the client device 12, the server device 18, and the departmental systems 22.

Patient records in the data storage unit 14 generally include any information related to a patient including, without limitation, biographical, financial, clinical, workflow, and care plan information. The patient records may be represented in a variety of file formats including, without limitation, text files such as documents, graphic files such as a graphical trace including, for example, an electrocardiogram (EKG) trace, an electrocardiogram (ECG) trace, and an electroencephologram (EEG) trace, video files such as a still video image or a video image sequence, an audio file such as an audio sound or an audio segment, and visual files, such as a diagnostic image including, for example, a magnetic resonance image (MRI), an x-ray, a positron emission tomography (PET) scan, or a sonogram. The patient record is an organized collection of clinical information concerning one patient's relationship to a healthcare enterprise (e.g. region, hospital, clinic, or department). The patient record can narrowly be considered as a file cabinet or repository with divisions and indexing mechanisms. These divisions resemble a hierarchy with folders, documents and document components, or other objects representing collections of clinical elementary information. Such folder divisions include traditional classifications such as summaries, notes, investigations, orders, medications, correspondence, results, etc. An individual information element and object resides in a home location in this structure. Revision history is captured from within this home location.

The first local area network (LAN) 16 provides a communication network among the client device 12, the data storage unit 14 and the server device 18. The second local area network (LAN) 20 provides a communication network between the server device 18 and the departmental systems 22. The first LAN 16 and the second LAN 20 may be the same or different LANs, depending on the particular network configuration and the particular communication protocols implemented. Alternatively, one or both of the first LAN 16 and the second LAN 20 may be implemented as a wide area network (WAN).

The communication paths 52, 56, 60, 62, 64, 66, 68 and 70 permit the various elements, shown in FIG. 1, to communicate with the first LAN 16 or the second LAN 20. Each of the communication paths 52, 56, 60, 62, 64, 66, 68 and 70 are preferably adapted to use one or more data formats, otherwise called protocols, depending on the type and/or configuration of the various elements in the healthcare information systems 10. Examples of the information system data formats include, without limitation, an RS232 protocol, an Ethernet protocol, a Medical Interface Bus (MIB) compatible protocol, DICOM protocol, an Internet Protocol (I.P.) data format, a local area network (LAN) protocol, a wide area network (WAN) protocol, an IEEE bus compatible protocol, and a Health Level Seven (HL7) protocol.

The I.P. data format, otherwise called an I.P. protocol, uses IP addresses. Examples of the I.P. addresses include, without limitation, Transmission Control Protocol Internet Protocol (TCPIP) address, an I.P. address, a Universal Resource Locator (URL), and an electronic mail (Email) address. The communication paths 52, 56, 60, 62, 64, 66, 68 and 70 each may be formed as a wired or wireless (W/WL) connection. The communication paths 52, 56, 60, 62, 64, 66, 68 and 70 may be formed as a wired connection. In the case of a wired connection, the I.P. address is preferably assigned to a physical location of the termination point of the wire, otherwise called a jack. The jack is mounted in a fixed location near the location of the various elements. In the case of a wireless connection, I.P. addresses are preferably assigned to the various elements, since the various elements would be mobile. The wireless connection permits the person using the healthcare information system 10 to be mobile beyond the distance permitted with the wired connection.

The server device 18 generally includes a processor 30, a memory unit 32, and patient treatment monitoring system 34. The memory unit 32 includes workflow data and a treatment plan 36 and a database 38 containing patient records. Patient treatment monitoring system 34 preferably includes a user interface 40 and Rules Engine and Workflow Engine (task scheduler) 42, but may also include processor 30 and memory unit 32. Server device 18 is may be implemented as a personal computer or a workstation. As previously mentioned, database 38 provides an alternate location for storing patient records, and user interface 40 is an alternate interface for a user. In the preferred embodiment of the present invention, patient treatment monitoring system 34 including task scheduler 42 is responsive to user interface 23 (of alternate patient monitoring system 24) in client device 12. In an alternative embodiment, patient treatment monitoring system 24, including task scheduler 25 is responsive to user interface 23 in client device 12.

Patient treatment monitoring system 34 performs analysis and variance processing and adaptively selects and schedules workflow tasks in response to an identified variance indicating a variation of patient treatment from planned treatment. Workflow data and treatment plan 36 comprises a repository containing treatment plan information for patients together with corresponding workflow data used for initiating scheduled tasks for implementing the treatment plans. A user is able to view current and past treatment plans for patients accessed from unit 36 via user interface 23. Orders placed for the patient, regardless of where the user enters them in the healthcare information system, are incorporated into the patient's overall treatment care plan and are accessible from workflow data and treatment plan 36. The treatment plan of unit 36 incorporates user entered patient progress data including performance and outcome information and provides test results and other outcome information associated with planned treatment activity as well as orders for a patient to a user via interface 23. The treatment plan of unit 36 includes an activity chart such as a Gantt chart, which is displayed in the same display window as a treatment plan. Further, a user is able to update and modify a treatment plan in unit 36. In addition, memory 32 provides data that integrates a patient medical record, the patient's treatment plan, and an activity chart.

Departmental systems 22 are systems that need access to information or provide information related to the health and/or welfare of patients in the care of the healthcare provider. Examples of the departmental systems 22 include, without limitation, a lab system 44, a pharmacy system 46, a financial system 48 and a nursing system 50, as shown in FIG. 1, but may also include a records system, a radiology system, an accounting system, a billing system, and any other system required or desired in a healthcare information system.

Figure 2:
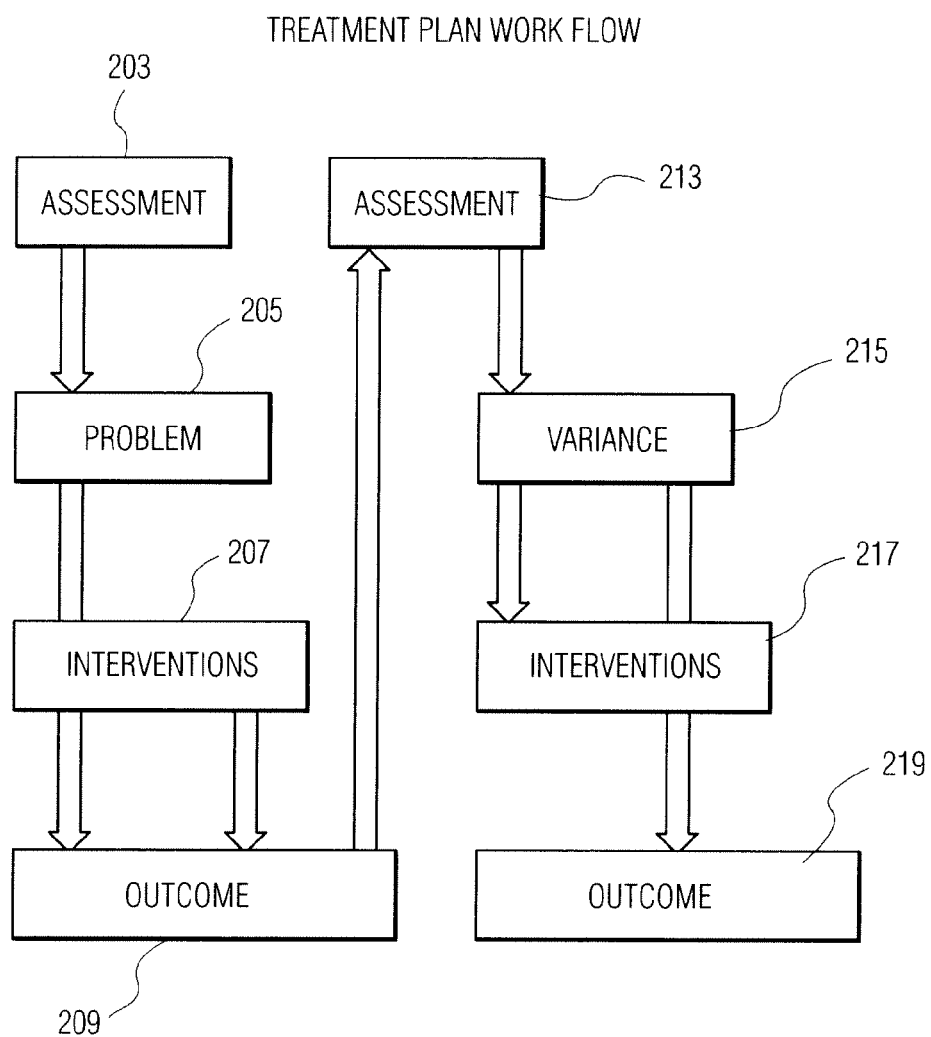
FIG. 2 shows a clinical workflow task sequence employed by a patient treatment management system, according to invention principles.

FIG. 2 shows a clinical workflow task sequence employed by a patient treatment management system. The data for implementing a workflow task sequence is stored in unit 36 of FIG. 1. A treatment plan workflow involves performance of a patient diagnosis in step 205 following a patient assessment in step 203. A treatment activity (an intervention) is performed in step 207 based on the diagnosis and a corresponding outcome is determined in step 209. The outcome is assessed in step 213 and a variance indicating a variation of patient treatment outcome from a planned treatment outcome is determined in step 215. The system advantageously enables a health care provider to document when there are deviations (variances) from a treatment plan and to record reasons for variances. This documentation and monitoring supports regulatory, audit and process improvement functions and enables an organization to demonstrate to regulatory agencies and legal entities that the healthcare organization is making a conscious effort to provide the best care possible and to improve processes. Treatment goals and expected outcomes are clinical objectives that are established for a patient in relation to identified problems. They are measurable and are expected to be achieved as a result of implementing interventions stated in a Treatment Plan. Target timeframes are assigned to the goals to monitor that patient condition improves at an accepted rate. A health care provider (HP) documents whether the goals are met within the timeframes indicated within the plan. A deviation from these expected outcomes is a variance and the reason for the identified variance is documented in the event that a goal is not achieved. A treatment activity (an intervention) is performed in step 217 in response to the determined variance and a resultant outcome determined in step 219. The process steps 213-219 are repeated as required.

The identification of treatment variances from a patient expected outcome provides a healthcare provider (e.g., nurses, case managers, dietitians, respiratory therapists, physical therapists and physicians typically responsible for performing the services required by a plan) with valuable information. Specifically, it enables a healthcare provider to determine how effective a treatment planning process for a patient has been and is usable by treatment planning management system 34 to prompt a user with an alert if interventions planned for the patient have not been completed or have not been completed in a timely manner. System 34 also alerts a healthcare provider of patterns and common issues that exist for a particular patient and prompts a user with suggestions for further evaluation of these issues. In addition, system 34 advantageously compares actual treatment outcomes with expected outcomes across patient populations to provide information used in evidence based practice standards development. The use of coded variances to document differences between actual and expected outcomes in this manner improves treatment analysis and reporting.

Figure 3:
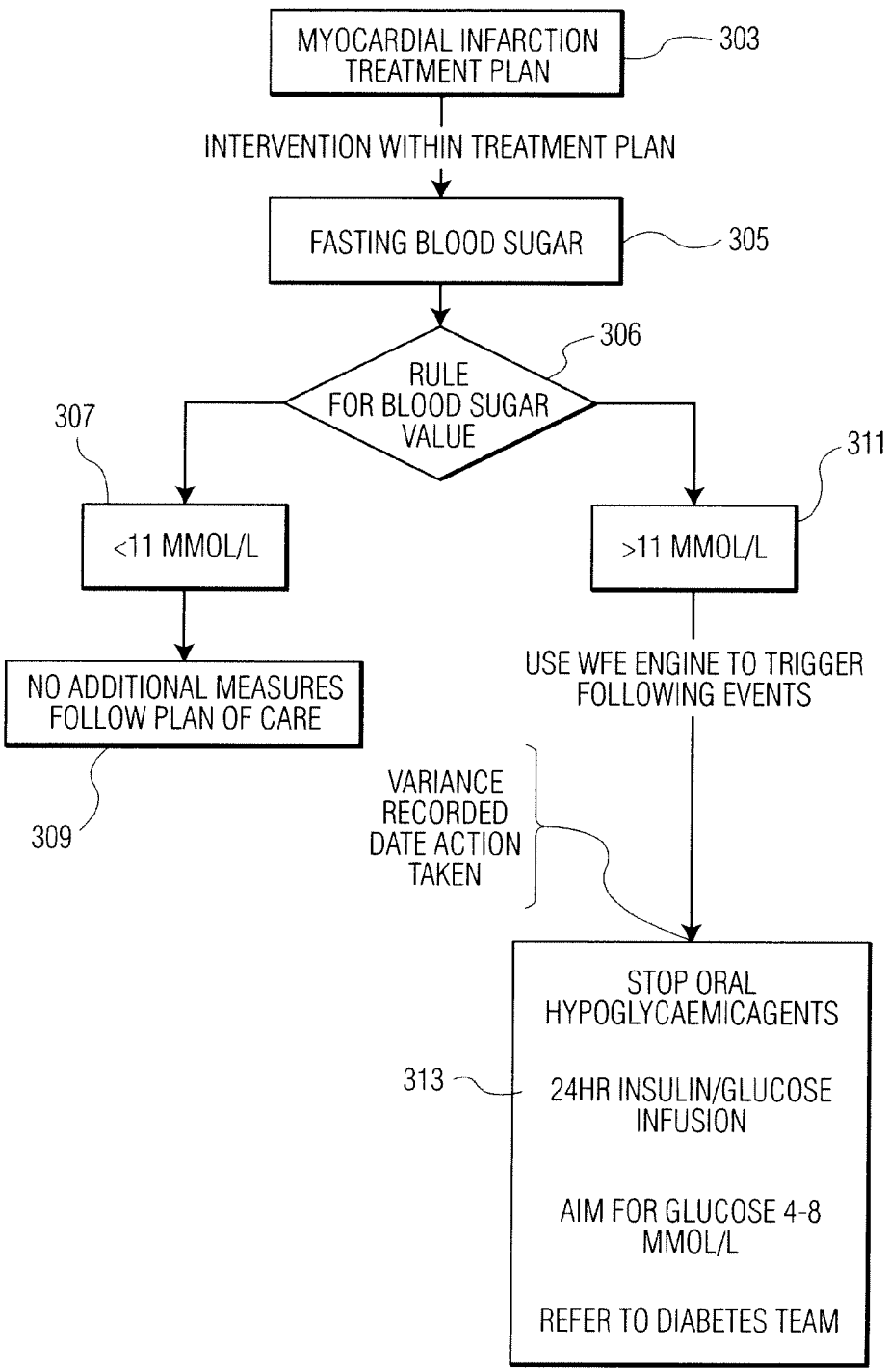
FIG. 3 shows a myocardial infarction clinical treatment workflow task sequence managed by a patient treatment management system, according to invention principles.

FIG. 3 shows a myocardial infarction clinical treatment workflow task sequence managed by patient treatment management system 34. The workflow of FIG. 3 is implemented by task scheduler 42 using workflow process rules and task sequencing instructions derived from unit 36. Rules retrieved from unit 36 are used to trigger an additional task sequence for treating a patient in the event of detection of abnormal blood sugar level and to document a variance within the treatment plan in unit. 36. Following initiation of an intervention action in step 303, a patient fasting blood sugar level is measured in step 305. Workflow rules from unit 36 are applied by task scheduler 42 in step 306 to initiate different task sequences depending on measured blood sugar level. If blood sugar level is below 11 MMOL, per liter in step 307 no additional measure are taken and the process stops at step 309. If blood sugar level is greater than or equal to 11 MMOL per liter in step 311, task scheduler 42 initiates recording and documentation of a treatment variance and recorded date and time of action taken and also initiates additional treatment tasks in step 313. Specifically, task scheduler 42 in step 313 instructs healthcare workers to terminate oral hypoglycaemic agents, administer a 24 hour insulin/glucose infusion with a target glucose level of 4-8 MMOL per liter and refers the patient for review by a specialist diabetes healthcare worker team. This terminates the FIG. 3 process.

Figure 4:
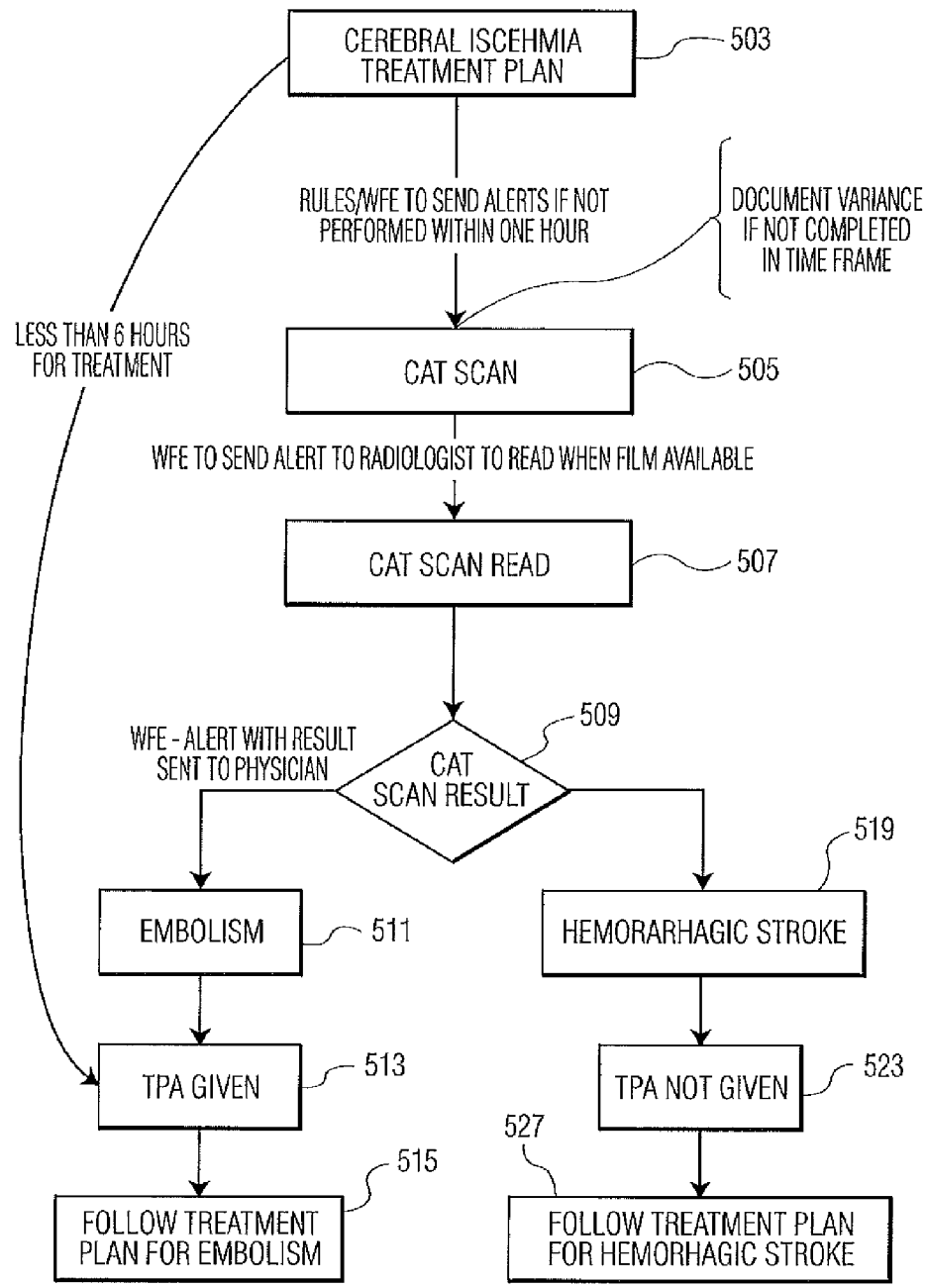
FIG. 4 shows a stroke clinical treatment workflow task sequence managed by a patient treatment management system, according to invention principles.

FIG. 4 shows a stroke clinical treatment workflow task sequence managed by patient treatment management system 34. In similar fashion to the process of FIG. 3, the workflow of FIG. 4 is implemented by task scheduler 42 using workflow process rules and task sequencing instructions derived from unit 36. Patient treatment management system 34 differs from typical existing Treatment Plan systems in the use of a Workflow Engine to manage complex Treatment Plan processes. A Workflow Engine (task scheduler 42) ensures the right work is given to the right person at the right time. Task scheduler 42 acts as a sentinel that is continuously alert and advantageously monitoring work schedules and action or inaction of multiple clinicians and other systems that occurs within predefined time periods. In addition task scheduler 42 concurrently monitors patient clinical information such as blood coagulation results, for example. Potentially any element in the FIG. 1 system can interact with task scheduler 42 via networked communication. If a variance in a Treatment Plan in unit 36 is detected, task scheduler 42 orchestrates steps to manage recovery. Unlike a Treatment Plan enhanced with a rules function, events managed by task scheduler 42 are coordinated in time and are active for the life of a Treatment Plan, whether the plan is active for minutes, hours, days, or years.

FIG. 4 illustrates an Acute Stroke Management Treatment Plan and application of task scheduler 42 within a Treatment Plan according to invention principles. Strokes are the number one cause of disability in adults. In the United States alone, 600,000 Americans suffer strokes each year. The disability in a patient with an embolic stroke may be prevented if a Thrombolytic agent (e.g., t-PA) is given within 6 hours of the start of symptoms. A desired outcome is to provide treatment to a patient with t-PA in less than 2 hours from when the patient reaches the door of emergency room (door-to-needle rate). To date, only 2% of eligible patients with embolic stroke receive t-PA agent within the 2 hour window. One reason for this poor performance is the fact that a Treatment Plan for the Acute Management of a Stroke Patient is complex and time sensitive, involving many members of an interdisciplinary team and delegation of duties. Consequently, healthcare organizations typically are unable to accomplish patient t-PA screening (stroke/t-PA assessment and CAT scan, radiology interpretation) and administration of t-PA within 6 hours from onset of symptoms.

Following initiation of an acute stroke treatment plan in step 503, a CAT scan is performed in step 505. Patient treatment management system 34 (including task scheduler 42) applies workflow rules from unit 36 to identify whether the CAT scan of step 505 has been performed within 1 hour of patient admission and initiates generation of an alert message to a user in response to a determination the CAT scan has not been performed within the predetermined period. System 34, further documents a variance in the treatment plan of unit 36 if the CAT scan was not performed within the predetermined period. Upon completion of the CAT scan in step 505, system 34 task scheduler 42 in step 507 initiates communication of an alert message to a radiologist prompting the radiologist to read and interpret the CAT scan as soon as it is available and enter results in the patient treatment management system 34. In response to received documented CAT scan results, task scheduler 42 of system 34 in step 509 initiates performance of steps 511-515 for treatment of an embolism or steps 519-527 for treatment of acute stroke. Specifically, task scheduler 42 in step 511 updates the treatment plan in unit 36 to indicate a received diagnosis of an embolism based on CAT scan results and informs a healthcare worker of the need to administer t-PA promptly in step 513. System 34 initiates performance of further embolism treatment activities, as determined by the treatment plan of unit 36, by healthcare workers in step 515.

Alternatively, based on results received in step 509, task scheduler 42 in step 519 updates the treatment plan in unit 36 to indicate a received diagnosis of an acute hemorrhagic stroke based on CAT scan results and informs a healthcare worker that t-PA is not to be administered in step 523. System 34 further initiates performance of hemorrhagic stroke treatment activities, as determined by the treatment plan of unit 36, by healthcare workers in step 527. The patient treatment management system 34 advantageously manages resources and healthcare personnel so that patients may be successfully treated with t-PA within a 6 hour window from onset of the condition. Successfully diagnosing and treating a patient within the 6 hour window has been found to be crucial in patient survival and this is advantageously facilitated by the workflow driven system of task scheduler 42 and system 34. Preferably, system 34 determines a patient is eligible to receive t-PA and ensures t-PA is administered to the patient within 2 hours of initiation of care and as a result ideally the patient will be free of complications. System 34 continuously monitors time from initiation of the patient medical condition to ensure t-PA is administered if required within the required treatment window.

System 34 (including task scheduler 42) together with treatment plan and workflow data unit 36, manages healthcare interventions (actions) by healthcare workers in performance of multiple additional tasks involved in treating acute stroke using t-PA, for example. These additional tasks include, initiating. Intravenous infusion (e.g. with an order of KVO with 0.9NSS—Order for 0.0.9% of normal saline solution and to Keep Vein Open), administering Oxygen (e.g., 2 Liters per minute), acquiring and monitoring Vital Signs (e.g., every 5 minutes until stable, then every is minutes). Typically intravenous access is started immediately upon arrival of a patient at an emergency department to support timely delivery of intravenous medications including t-PA for treatment of embolic stroke. Other tasks include, initiating Emergency Neurological Triage Evaluation and National Institute of Health Stroke assessment, initiating Blood Glucose measurement, an immediate Platelet Count measurement (a blood clotting indicator), an immediate APTT measurement (used to monitor anti coagulation therapy with such agents as heparin, for example) and an interventional Radiology Consultation, for example. The National Institute of Health Stroke Assessment is a standardized assessment instrument which includes both patient history and physical assessment questions with the intent of assessing patient neurological and medical status.

Figure 5:
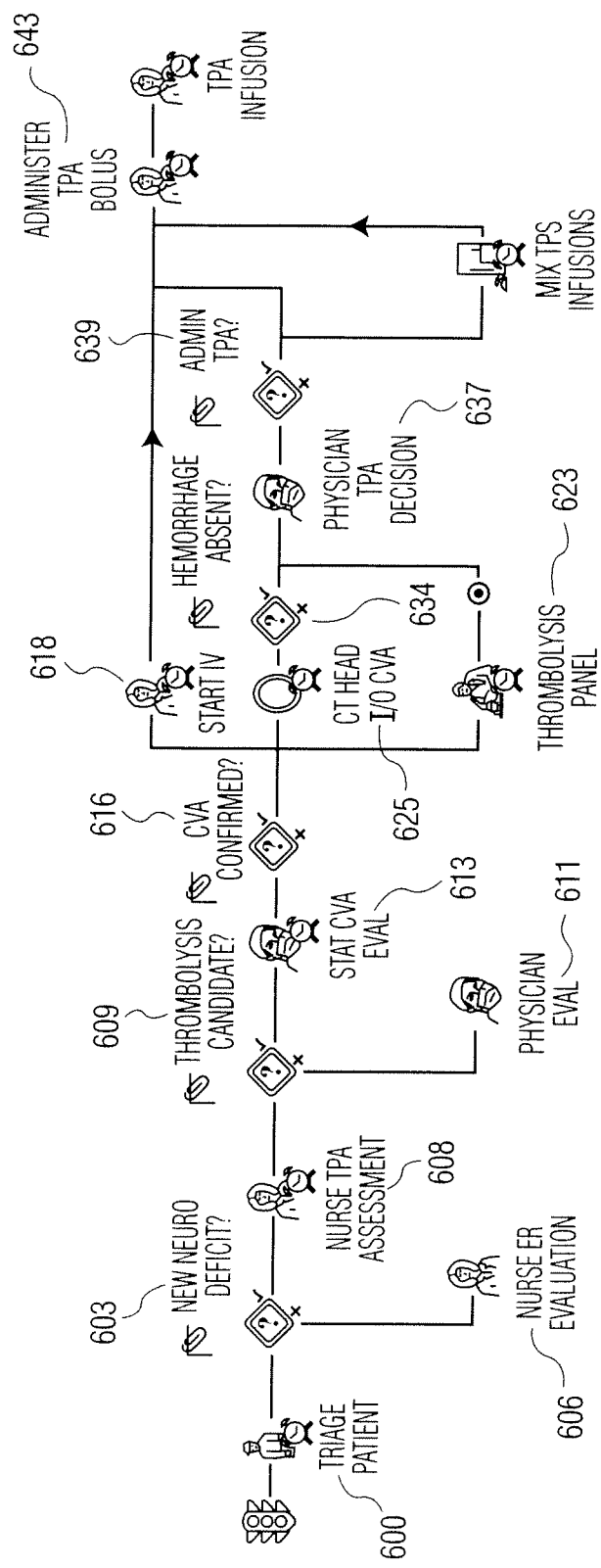
FIG. 5 illustrates a stroke clinical treatment workflow, according to invention principles.

FIG. 5 further shows an acute stroke clinical treatment workflow process. The Workflow process illustrates integration of operation of task scheduler 42 with a Treatment Plan accessed from unit 36 to facilitate rapid identification of patients who are candidates for t-PA and to prevent bottlenecks in patient care. In the workflow process task scheduler 42 monitors performance, of an action or lack of action according to treatment plan schedule. For example, if the CAT scan in the Acute Stroke Management Treatment Plan of FIG. 4 is not completed within a defined time period, appropriate staff are notified of the delay to evaluate and intervene, ultimately preventing treatment variances from occurring. A patient is given a neurological deficit examination in step 603, following an initial emergency examination in step 600 and if no neurological deficit is found, a nurse performs an emergency room appropriateness evaluation in step 606. If a neurological deficit is found, a nurse makes a t-PA suitability assessment in step 608 and if in step 609 it is determined the patient is not a thrombolysis candidate, a physician evaluation of the patient is performed in step 611. If in step 609 it is determined the patient is a thrombolysis candidate, a CVA Cerebrovascular Accident (CVA), evaluation is performed in step 613 and if CVA is confirmed in step 616 an IntraVenous (IV) infusion is administered in step 618, a panel of thrombolysis test is performed in step 623 and a CT scan is performed in step 625. If it is determined using the CT scan in step 634 that hemorrhage is absent, a physician decides whether t-PA is to be administered in steps 637 and 639 using the test panel results and CT scan. If t-PA is to be administered, a t-PA infusion is prepared in step 641 and administered in steps 643 and 647.

Figure 6:
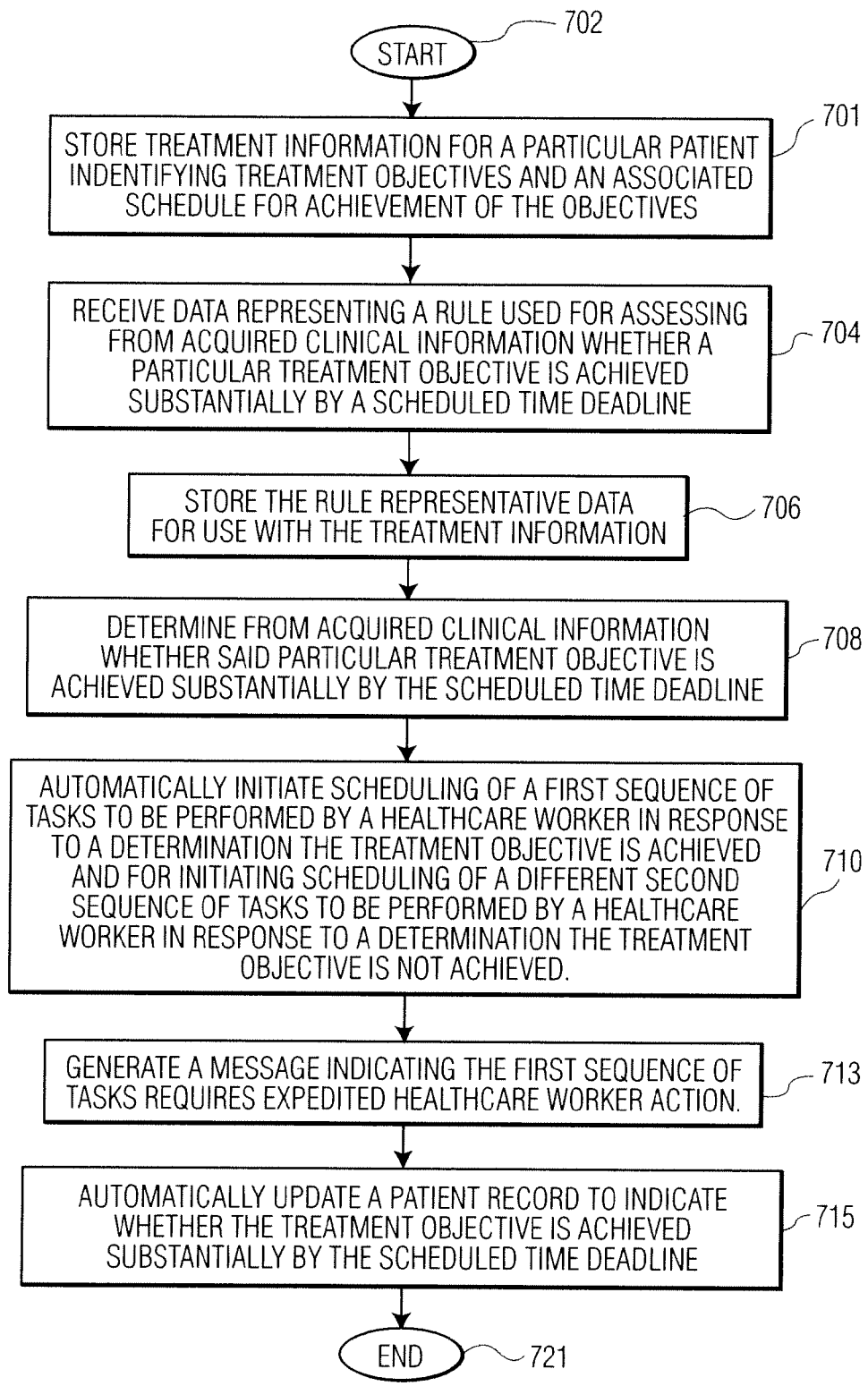
FIG. 6 shows a flowchart of a process for patient treatment management, according to invention principles.

FIG. 6 shows a flowchart of a process employed by system 34 (FIG. 1) for patient treatment management. In Step 702, following the start at step 701, system 34 stores treatment information in unit 36 for a particular patient identifying treatment objectives and an associated schedule for achievement of the objectives. In step 704 system 34 receives data representing a rule used for assessing from acquired clinical information whether a particular treatment objective is achieved substantially by a scheduled time deadline. The data representing the rule is acquired in response to user data entry via a displayed user interface image menu provided by a display generator. Further, the treatment information in unit 36 comprises a treatment plan for the particular patient and the rule is incorporated as part of the plan within unit 36. System 34 acquires the data representing clinical information of the particular patient from a clinical information system (of unit 22) such a laboratory test result processing system, a medication administration information system and a clinician order processing system. System 34 may also acquire the data representing clinical information of the particular patient via data entry at a point of care comprising a care station, patient room or examination room, for example. In step 706 system 34 stores the rule representative data for use with the treatment information and in step 708 determines from acquired clinical information whether the particular treatment objective is achieved substantially by the scheduled time deadline. System 34 determines, for example, from the acquired clinical information, whether or not a procedure required by the treatment plan has been performed substantially by the scheduled time deadline.

System 34 in step 710 automatically initiates scheduling of a first sequence of tasks to be performed by a healthcare worker in response to a determination the treatment objective is achieved. System 34 initiates scheduling of a different second sequence of tasks to be performed by a healthcare worker (and initiates communication of an alert message to the healthcare worker) in response to a determination the treatment objective is not achieved. Such a data treatment objective is not achieved in response to a failure to acquire data representing clinical information of the particular patient related to the particular treatment objective, substantially by the scheduled time deadline, for example. In step 713 system 34 generates a message indicating the first sequence of tasks requires expedited healthcare worker action and automatically updates the treatment plan for the particular patient in unit 38 in step 715 to record whether the particular treatment objective is achieved substantially by the scheduled time deadline.

The system and processes presented in FIGS. 1-6 are not exclusive. Other systems and processes may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. Further, any of the functions provided by the system of FIG. 1 may be implemented in hardware, software or a combination of both.

What is claimed is:

1. A patient treatment management system, comprising:
    a repository including treatment information for a particular patient identifying treatment objectives and an associated schedule for achievement of said objectives;
    an interface processor for acquiring data representing clinical information of a particular patient related to a particular treatment objective;
    a monitoring processor for automatically assessing from the acquired clinical information whether said particular treatment objective is achieved substantially by a scheduled time deadline in response to an identified variance indicating a variation of patient treatment from planned treatment; and a task scheduling processor for automatically initiating scheduling of a first sequence of tasks to be performed by a healthcare worker in response to a determination said particular treatment objective is achieved and for initiating scheduling of a different second sequence of tasks to be performed by a healthcare worker in response to a determination said particular treatment objective is not achieved.

2. A system according to claim 1, wherein
said identified variance comprises a selected one of a plurality of predefined coded variances documenting differences between actual and expected outcomes,
said monitoring processor determines, from said acquired clinical information, a treatment procedure required by said treatment information has not been performed substantially by said scheduled time deadline and
said task scheduling processor automatically initiates scheduling of said first sequence of tasks to be performed by a healthcare worker in response to said determination said treatment procedure has not been performed substantially by said scheduled time deadline.

3. A system according to claim 2, wherein
said task scheduling processor generates a message indicating said first sequence of tasks requires expedited healthcare worker action and
said treatment information comprises a treatment plan for said particular patient identifying expected outcome of treatment and an associated schedule for achievement of said objectives and care actions a healthcare team need to take to reach these expected outcomes.

4. A system according to claim 1, including
a documentation processor for automatically updating a patient record to indicate whether said treatment objective is achieved and
said task scheduling processor acts as a sentinel that is continuously alert and monitoring work schedules and action and inaction of multiple clinicians and other systems that occurs within predefined time periods and initiates scheduling of a sequence of tasks in response to a detected action or inaction.

5. A system according to claim 1, including
a documentation processor for automatically updating said treatment information to record whether said particular treatment objective is achieved substantially by said scheduled time deadline.

6. A system according to claim 1, wherein
said treatment information comprises a treatment plan for said particular patient and
said monitoring processor compares actual treatment outcomes with expected outcomes determined from treatment data of a patient population and
said task scheduling processor initiates scheduling of a sequence of tasks in response to the comparison.

7. A system according to claim 1, wherein
said interface processor acquires said data representing clinical information of said particular patient via data entry at a point of care comprising at least one of, (a) a care station, (b) patient room and (c) examination room.

8. A system according to claim 1, wherein
said interface processor acquires said data representing clinical information of said particular patient from a clinical information system comprising at least one of, (a) a laboratory test result processing system, (b) a medication administration information system and (c) a clinician order processing system.

9. A system according to claim 1, wherein
said first sequence of tasks and said different second sequence of tasks are alternatively performed by said healthcare worker to provide a treatment to said particular patient selected in response to whether or not said particular treatment objective is achieved substantially by said scheduled time deadline.

10. A system according to claim 1, wherein
a treatment objective comprises a treatment result and
said task scheduling processor automatically initiates scheduling of a first sequence of tasks to be performed by a healthcare worker in response to a determination a first treatment result is achieved and initiates scheduling of a different second sequence of tasks to be performed by a healthcare worker in response to a determination a second treatment result is achieved.

11. A system according to claim 1, wherein
said task scheduling processor automatically initiates scheduling of a first sequence of tasks to be performed by a healthcare worker in response to said interface processor failing to acquire, data representing clinical information of said particular patient related to said particular treatment objective, substantially by said scheduled time deadline.

12. A system according to claim 1, wherein
said task scheduling processor automatically initiates generation of an alert message for communication to a healthcare worker in response to said interface processor failing to acquire, data representing clinical information of said particular patient related to said particular treatment objective, substantially by said scheduled time deadline.

13. A patient treatment management system, comprising:
a repository including treatment information for a particular patient identifying expected results of treatment, care actions a healthcare team need to take to reach said expected results and an associated schedule for achievement of said expected results;
an interface processor for acquiring data representing clinical information of a particular patient related to a particular treatment result;
a monitoring processor for automatically assessing from the acquired clinical information whether said particular treatment result is achieved substantially by a scheduled time deadline in response to an identified coded variance indicating a variation of patient treatment from planned treatment selected from a plurality of predefined coded variances documenting differences between actual and expected outcomes; and
a task scheduling processor for substantially continuously monitoring work schedules and action and inaction of multiple clinicians and other systems that occurs within predetermined time periods and initiating scheduling of a sequence of tasks in response to a detected action or inaction and for automatically initiating scheduling of a first sequence of tasks to be performed by a healthcare worker in response to a determination a first treatment result is achieved and for initiating scheduling of a different second sequence of tasks to be performed by a healthcare worker in response to a determination a second treatment result is achieved.

14. A system for generating a patient treatment management plan, comprising:
a repository including treatment information for a particular patient identifying treatment objectives, care actions to be taken to reach said objectives and an associated schedule for achievement of said objectives;

an interface processor for receiving data representing a rule used for assessing from acquired clinical information whether a particular treatment objective is achieved substantially by a scheduled time deadline and for storing the rule representative data for use with said treatment information;

a monitoring processor for assessing from acquired clinical information whether said particular treatment objective is achieved substantially by said scheduled time deadline in response to an identified variance indicating a variation of patient treatment from planned treatment selected from a plurality of predefined coded variances documenting differences between actual and expected outcomes; and a task scheduling processor for substantially continuously monitoring work schedules and action and inaction of multiple clinicians and other systems that occurs within predetermined time periods and initiating scheduling of a sequence of tasks in response to a detected action or inaction and for automatically initiating scheduling of a first sequence of tasks to be performed by a healthcare worker in response to a determination said treatment objective is achieved and for initiating scheduling of a different second sequence of tasks to be performed by a healthcare worker in response to a determination said treatment objective is not achieved.

15. A system according to claim 14, including
a display generator for initiating generation of a user interface image menu enabling a user to enter data representing said rule.

16. A system according to claim 14, wherein
said treatment information comprises a treatment plan for said particular patient and said rule is incorporated as part of said plan.

17. A patient treatment management system, comprising:
a repository including treatment information for a particular patient identifying results of treatment, care actions to be taken to reach said results and an associated schedule for achievement of said treatment results;

an interface processor for acquiring data representing clinical information of a particular patient related to a particular treatment result;

a monitoring processor for assessing from the acquired clinical information whether said particular treatment result is achieved substantially by said scheduled time deadline in response to an identified coded variance indicating a variation of patient treatment from planned treatment; and a task scheduling processor for substantially continuously monitoring work schedules and action and inaction of multiple clinicians and other systems that occurs within predetermined time periods and initiating scheduling of a sequence of tasks in response to a detected action or inaction and for automatically initiating scheduling of a first sequence of tasks to be performed by a healthcare worker in response to a determination a first treatment result is achieved and for initiating scheduling of a different second sequence of tasks to be performed by a healthcare worker in response to a determination a second treatment result is achieved.

18. A patient treatment management system, comprising:
a repository including treatment information for a particular patient identifying treatment objectives, care actions to be taken to reach said objectives and an associated schedule for achievement of said objectives;

an interface processor for acquiring data representing clinical information of a particular patient related to a particular treatment objective;

a monitoring processor for determining, from the acquired clinical information, whether a procedure required by said treatment information has been performed substantially by a scheduled time deadline in response to an identified variance indicating a variation of patient treatment from planned treatment selected from a plurality of predefined coded variances documenting differences between actual and expected outcomes; and a task scheduling processor for substantially continuously monitoring work schedules and action and inaction of multiple clinicians and other systems that occurs within predetermined time periods and initiating scheduling of a sequence of tasks in response to a detected action or inaction and for automatically initiating scheduling of a first sequence of tasks to be performed by a healthcare worker in response to a determination said procedure has not been substantially performed by said scheduled time deadline and for initiating scheduling of a different second sequence of tasks to be performed by a healthcare worker in response to a determination said procedure has been performed substantially by said scheduled time deadline.

19. A method for managing patient treatment, comprising the activities of:
employing at least one computer for,
storing treatment information for a particular patient identifying treatment objectives and an associated schedule for achievement of said objectives;
acquiring data representing clinical information of a particular patient related to a particular treatment objective;
automatically determining from said acquired clinical information whether said particular treatment objective is achieved substantially by a scheduled time deadline in response to an identified variance indicating a variation of patient treatment from planned treatment; and
automatically initiating scheduling of a first sequence of tasks to be performed by a healthcare worker in response to a determination said treatment objective is achieved and for initiating scheduling of a different second sequence of tasks to be performed by a healthcare worker in response to a determination said treatment objective is not achieved.

20. A method for generating a patient treatment management plan, comprising the activities of:
employing at least one computer for,
storing treatment information for a particular patient identifying treatment objectives, care actions a healthcare team need to take to reach said objectives and an associated schedule for achievement of said objectives;
receiving data representing a rule used for assessing from acquired clinical information whether a particular treatment objective is achieved substantially by a scheduled time deadline;
storing said rule representative data for use with said treatment information;
determining from acquired clinical information whether said particular treatment objective is achieved substantially by said scheduled time deadline in response to an identified coded variance indicating a variation of patient treatment from planned treatment selected from a plurality of predefined coded variances documenting differences between actual and expected outcomes;

substantially continuously monitoring work schedules and action and inaction of multiple clinicians and other systems that occurs within predetermined time periods and initiating scheduling of a sequence of tasks in response to a detected action or inaction; and automatically initiating scheduling of a first sequence of tasks to be performed by a healthcare worker in response to a determination said treatment objective is achieved and for initiating scheduling of a different second sequence of tasks to be performed by a healthcare worker in response to a determination said treatment objective is not achieved.

* * * * *